Figure 1:
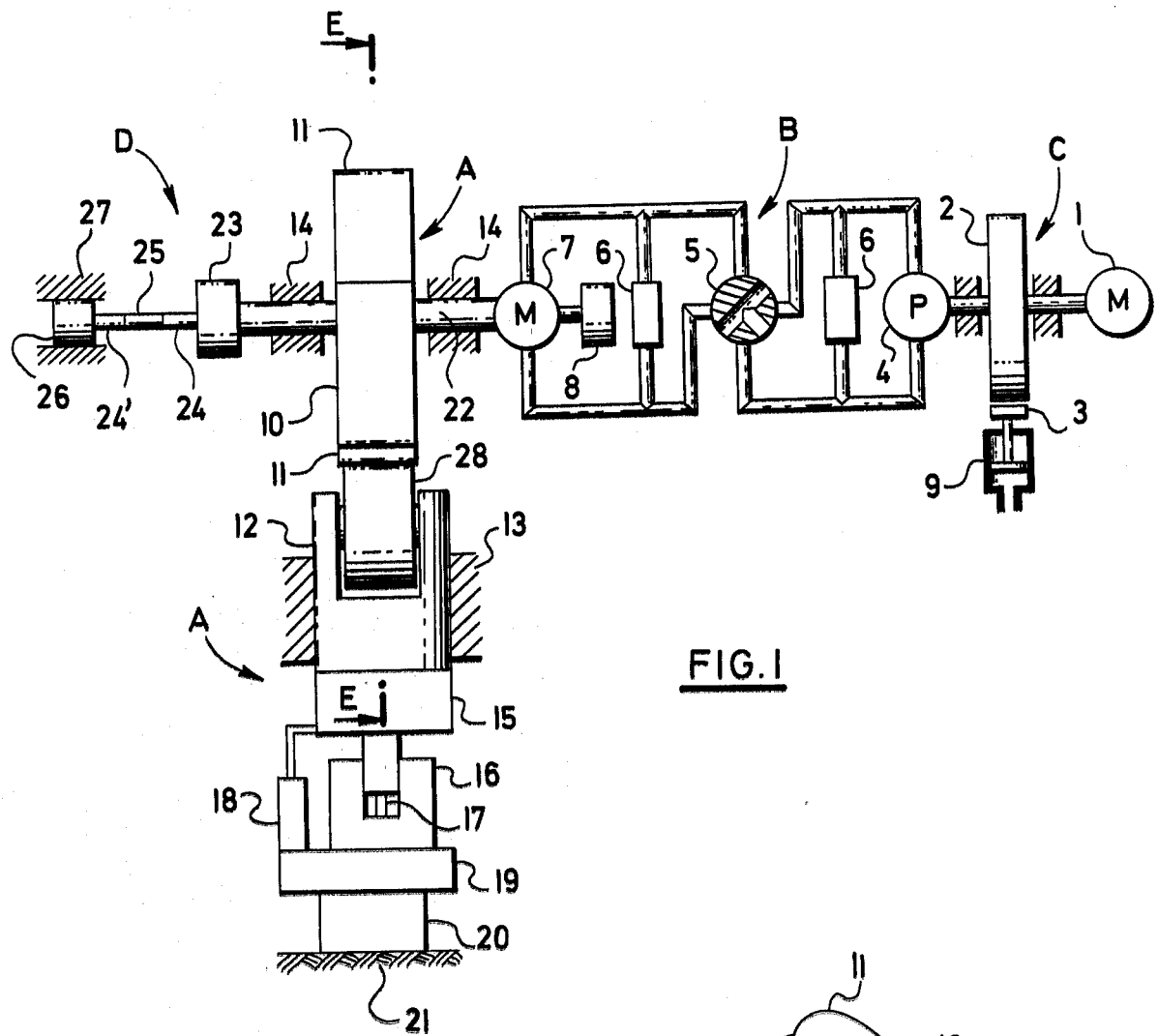

United States Patent

Fuxa

[11] 4,109,516
[45] Aug. 29, 1978

[54] CAM PLASTOMETER
[75] Inventor: Jan Fuxa, Ostrava, Czechoslovakia
[73] Assignee: Vyzkumny ustav hutnictvi zeleza, Dobra, Czechoslovakia
[21] Appl. No.: 780,315
[22] Filed: Mar. 23, 1977
[30] Foreign Application Priority Data
Apr. 2, 1976 [CS] Czechoslovakia ............... 2148/76
[51] Int. Cl.² .................................... G01N 3/00
[52] U.S. Cl. ........................................... 73/93
[58] Field of Search ............... 73/93, 94, 99, 90
[56] References Cited
U.S. PATENT DOCUMENTS

| | | | |
|---|---|---|---|
| 2,427,796 | 9/1947 | MacDonald | 73/99 |
| 2,885,888 | 5/1959 | Kutanchik et al. | 73/93 |
| 3,277,700 | 10/1966 | Myerholtz | 73/99 |
| 3,772,913 | 11/1973 | Zell et al. | 73/99 |
| 3,994,157 | 11/1976 | Burk et al. | 73/94 |

*Primary Examiner*—Anthony V. Ciarlante
*Attorney, Agent, or Firm*—Burgess, Ryan and Wayne

[57] ABSTRACT

A cam plastometer in which deformation compressive forces are applied to a specimen by a cam follower engaging a cam which is rotated by a hydraulic motor. By rotating the motor at a predetermined speed, and employing a particular profile of the cam periphery, deformation forces can be applied which vary with time in a desired manner, to simulate actual conditions which occur during industrial pressing and forming operations. The plastometer also is capable of torsional testing of specimens.

1 Claim, 2 Drawing Figures

CAM PLASTOMETER

The invention relates to a cam plastometer which permits the selection of the times of the interruption of the application of deformation forces in a multistage deformation process of a specimen tested. The plastometer simulates the conditions in which the material deformed stays during a manufacturing process, but can also be adapted at the same time for other tests of the specimen.

The plastometers known up to now do not satisfactorily simulate the production forming process as they do not match actual the deformation courses, deformation speeds, temperatures, stress states and times of deformation interruptions. For these reasons it is difficult to determine the characteristics of materials, such as resistance to deformation, formability and limit deformations, especially in hot forming. Known designs of plastometers make use of either the principle of controlling the movement of a hydraulic cylinder whose piston rod mechanically coupled to a jaw deforms the specimen — this principle is applied in hydraulic tensile stress test machines — or the deformation is produced by a rotating cam pushing a roller coupled mechanically to the jaw deforming the specimen. Cam plastometers are designed on this principle.

The hydraulic tensile test machines cannot obtain a sufficiently wide range of deformation speeds, which is a distinct limitation especially for tests in hot condition; the phenomena of strain hardening, recrystallization and similar effects cannot be fully examined; thus the forming characteristics obtained are incomplete.

Cam plastometers are capable of providing a wide range of deformation speeds, but they cannot readily provides multistage deformations of the specimen, and the deformation speed cannot be brought into agreement with the times of interruption between deformations. This again limits the ability to simulate a manufacturing process for a reliable determination of the forming characteristics of the materials tested.

The drawbacks stated above are eliminated to a substantial extent by the cam plastometer according to the present invention, the principle of which lies in that it comprises a disc having at least two firmly attached cams and a shaft coupled to a hydraulic transmitter connected to a drive, the disc being connected by a linkage between cam and roller to a follower equipped with a jaw. The invention furthermore comprises an arrangement wherein the disc is fitted with a shaft coupled to a torsion jaw of a torsion device.

According to another feature of the invention the cam plastometer is equipped with a mechanism for regulating the revolutions of the hydromotor comprising a pump and a distributor.

The cam plastometer according to the invention, by starting, rotating, braking and reversing the disc with cams to, is capable of providing, on the specimen for the upsetting test, selected times of deformation interruptions, to realize several deformations with generally selectable courses of the deformation and deformation speeds (by suitably selecting the contours of the cams and respective angular speeds of rotation of the disc), within a wide range of selections of the deformation speeds. The connection of the torsion device to the disc shaft is of advantage because it reduces the cost of the drive of the torsion plastometer and widens the possible uses of the plastometer according to the invention in the field of simulating stress conditions.

Figure 2:
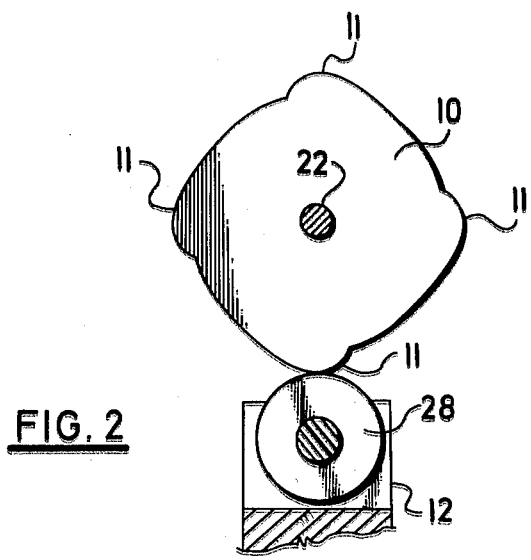

An example of an embodiment of the cam plastometer according to the present invention is illustrated diagrammatically in the annexed drawing in which FIG. 1 shows the kinematic plan of the cam plastometer and FIG. 2 illustrates a part section through plane E — E from FIG. 1 in the disc with cams and follower.

The cam plastometer according to the invention comprises an upsetting portion A, hydraulic transmitter B, drive C and torsion device D.

The upsetting portion A comprises a shaft 22 mounted in bearings 14 and rigidly connected to a disc 10 on the circumference of which are rigidly but interchangeably mounted cams 11 which by rolling push away a follower 12. The rectilinear motion of the follower 12 having at its end a jaw 15 is limited by a guide 13. In the jaw 15 and in the measuring jaw 19 is mounted the deformation sensor 18 and between the jaw 15 and the measuring jaw 19 is placed a container 16 housing the specimen 17 for the upsetting test. In the measuring jaw 19 is built in a sensor 20 for the deformation force and is rigidly attached to a support 21.

The hydraulic transmitter B comprises a regulation pump 4 connected via a threeway distributor 5 to a hydromotor 7 having a through shaft of lesser diameter firmly connected to a coding disc 8. The regulation pump 4 and the hydromotor 7 are equipped with safety and filling circuits 6.

The drive C comprises a motor 1 firmly connected to a flywheel 2 which has its circumference adapted for application of a brake 3 actuated by a hydraulic cylinder 9.

The torsion device D comprises a torsion spring, bar or other torsion device 23 in which is rigidly but interchangeably mounted a clamp 24 attached firmly to one end of the specimen 25 the other end of the specimen being finaly connected to another clamp 24 which is mounted rigidly but interchangeably in the torsion measuring jaw 26 the movement of which is limited by a frame 27.

The upsetting portion A is by means of the shaft 22 rigidly connected to the hydromotor 7 at the hydraulic transmitter B and to the torsion jaw 23 of the torsion device D. The drive C is rigidly connected to the shaft of the regulation pump 4 of the hydraulic transmitter B.

The hydraulic transmitter B permits rapid starting, stopping or reversing of the disc 10, the regulation pump 4 of the hydraulic transmitter B permits the selection within a wide range of the angular speed of rotation of the disc 10 and thus in relation to the shape of the cams 11 the selection within a wide range of the progressive speed of the follower 12 and thus the selection of a wide range of deformation speeds in upsetting the specimen 17.

The variable preselectable interruptions of the deformation are obtained by controlling the rotation of the disc 10 — by rapid braking of the disc 10 after realization of the deformation and starting the disc 10 for further deformation after elapse of the selected time. With higher deformation speeds to which correspond higher angular speeds of rotation of the disc 10 and thus also greater angles for the start or braking of the disc 10, the variable selectable times of deformation interruptions are realized by rapid braking of the disc 10, subsequent reversal, braking during the reverse motion of the disc 10 and restarting until engagement of the corresponding cam 11 with the follower 12 after elapse of the selected time. The impulses for controlling the movement of the disc 10 are obtained by comparing the position of the coding disc 8 with fed — in values of positions and by comparing the real time from the beginning of measurement with preselected times of deformation interruptions. In this way are simulated the course of deformations, deformation speeds and times of deformation interruptions of the deformation process on the specimen 17 during upsetting. The required temperature of the specimen 17 is obtained in that the specimen 17 with the container 16 is heated separately in a furnace; before the measurement it is placed in the container 16 between the jaw 15 and the measuring jaw 19.

The same principle of control of the motion of the disc 10 as in upsetting is applied in torsion tests. The required deformation of the specimen 25 is obtained in this case by a corresponding number of revolutions of the torsion jaw 23 relative to the torsion measuring jaw 26 the rotation of which is prevented by the frame 27. The deformation speed is obtained by selection of the corresponding angular speed of rotation of the torsion jaw 23, the deformation interruptions are realized by braking the rotary motion of the torsion jaw 23, i.e. by braking the disc 10.

Whether during control of the motion of the disc 10 a start, rotation at constant angular speed, braking or reversal takes place depends on the momentary position of the distributor 5 and on whether the disc 10 during shifting of the distributor is idle or in which direction it rotates. The heating of the specimen 25 in the torsion test may take place like in the upsetting test or by induction or indirectly by electric current.

The cam plastometer according to the invention enables the simulation with substantially increased accuracy, of the manufacturing process on a specimen of material in that it enables more precise control of the application of deformation forces and of deformation speeds and permits at the same time the maintenance of deformation interruptions even in upsetting tests. By attaching a torsion device D, one driving unit comprising a hydraulic transmitter B and a drive C is saved and the application field of the cam plastometer according to the invention is widened to including partial simulation of stress conditions of forming processes. The cam plastometer according to the invention enables the determination of deformation resistances, formability characteristics and limit deformations for use in projecting and designing, e.g., energy and force parameters, and for the requirements of physics and metallurgy such as the development of new materials, testing of materials, research in the phenomena of strain hardening, restoration, recrystallization or diffusion, grain growth etc.

I claim:

1. A dynamic cam plastometer for simulating multiple deformation processes, comprising:
    a rotatable disc cam having a plurality of peripheral lobes;
    a first shaft for rotating said disc;
    a second shaft coupled for rotation with said first shaft;
    a torsion element connected to said second shaft;
    a hydromotor connected to said first shaft for rotating said shafts and said disc in accordance with a hydraulic control signal corresponding to the magnitude and direction of the desired shaft rotation for rotating said first shaft through a predetermined number of revolutions in accordance with a preset deformation vs. time profile;
    a hydraulic control circuit for generating said control signal, said circuit comprising programming means including a coding disc coupled to said first shaft, a regulating pump and a hydraulic distributor coupled between said pump and said hydromotor;
    means for disposing a first specimen to be tested between said torsion element and a fixed support;
    a cam follower comprising a roller contacting the periphery of said disc, and a displaceable follower element coupled to the roller for linear movement in response to rotation of said cam;
    a rigid jaw coupled to said follower element; and
    means for disposing a second specimen to be tested between said jaw and a fixed rigid surface.

* * * * *

UNITED STATES PATENT OFFICE
CERTIFICATE OF CORRECTION

Patent No. 4,109,516     Dated August 29, 1978

Inventor(s) Jan Fuxa

It is certified that error appears in the above-identified patent and that said Letters Patent are hereby corrected as shown below:

Column 1, line 5: "the" (3rd occurrence) should be cancelled.

line 59: "to" should be cancelled.

Column 2, line 39: "finaly" should be --finally--.

Column 3, line 2: "The impulses" should start a new paragraph.

*Signed and Sealed this*

*Twenty-ninth* Day of *May 1979*

[SEAL]

Attest:

RUTH C. MASON
*Attesting Officer*

DONALD W. BANNER
*Commissioner of Patents and Trademarks*